(12) United States Patent
Uribe et al.

(10) Patent No.: US 7,671,340 B2
(45) Date of Patent: Mar. 2, 2010

(54) ADJUSTABLE-FOCAL-LENGTH COLLIMATORS METHOD AND SYSTEM

(75) Inventors: Jorge Uribe, Niskayuna, NY (US);
Floribertus P. M. Heukensfeldt Jansen, Ballston Lake, NY (US); James William Hugg, Glenville, NY (US)

(73) Assignee: General Electric Company, Niskayuna, NY (US)

( * ) Notice: Subject to any disclaimer, the term of this patent is extended or adjusted under 35 U.S.C. 154(b) by 59 days.

(21) Appl. No.: 11/778,290

(22) Filed: Jul. 16, 2007

(65) Prior Publication Data
US 2009/0022278 A1    Jan. 22, 2009

(51) Int. Cl.
*G21K 1/02* (2006.01)
(52) U.S. Cl. .................................................. 250/363.1
(58) Field of Classification Search ............... 250/363.1
See application file for complete search history.

(56) References Cited

U.S. PATENT DOCUMENTS

| | | | |
|---|---|---|---|
| 4,289,965 A | 9/1981 | Koga | |
| 4,389,569 A | 6/1983 | Hattori | |
| 5,032,728 A | 7/1991 | Chang | |
| 5,273,043 A * | 12/1993 | Ruike | ..................... 600/436 |
| 5,453,623 A | 9/1995 | Wong | |
| 5,825,031 A | 10/1998 | Wong | |
| 6,504,157 B2 | 1/2003 | Juhi | |
| 6,525,320 B1 | 2/2003 | Juni | |
| 6,525,321 B2 | 2/2003 | Juni | |
| D474,277 S | 5/2003 | Juni | |
| 6,744,053 B2 | 6/2004 | Wong | |
| D492,998 S | 7/2004 | Juni | |
| 6,794,653 B2 | 9/2004 | Wainer | |
| 6,906,330 B2 | 6/2005 | Blevis | |
| 7,012,257 B2 | 3/2006 | Juni | |
| 7,015,476 B2 | 3/2006 | Juni | |
| 7,071,473 B2 | 7/2006 | Juni | |
| 7,102,138 B2 | 9/2006 | Belvis | |
| 7,105,825 B2 | 9/2006 | Juni | |
| 7,138,638 B2 | 11/2006 | Juni | |
| 2004/0239941 A1 | 12/2004 | Schramm | |
| 2005/0205795 A1 | 9/2005 | Blevis | |

(Continued)

FOREIGN PATENT DOCUMENTS

WO    WO 2005/006977    1/2005

(Continued)

OTHER PUBLICATIONS

U.S. Appl. No. 11/731,856, filed Mar. 30, 2007.

(Continued)

*Primary Examiner*—David P Porta
*Assistant Examiner*—Marcus H Taningco
(74) *Attorney, Agent, or Firm*—Scott J. Asmus

(57) ABSTRACT

Embodiments relate to an imaging system that includes a collimator assembly having one or more pinhole apertures therein. The imaging system is configured so that one or more of the pinhole apertures has an adjustable focal length. The imaging system further includes a detector assembly configured to generate one or more signals in response to gamma rays that pass through the one or more pinhole apertures. Embodiments also relate to methods of changing collimator performance and methods of imaging a volume.

26 Claims, 10 Drawing Sheets

U.S. PATENT DOCUMENTS

| | | |
|---|---|---|
| 2006/0050845 A1 | 3/2006 | Juni |
| 2006/0118730 A1 | 6/2006 | Hefetz |
| 2006/0192308 A1 | 8/2006 | Juni |
| 2007/0007455 A1 | 1/2007 | Juni |
| 2007/0221853 A1* | 9/2007 | Joung .................... 250/363.09 |
| 2008/0001088 A1* | 1/2008 | Joung ...................... 250/363.1 |

FOREIGN PATENT DOCUMENTS

| | | |
|---|---|---|
| WO | WO 2006/029163 | 3/2006 |

OTHER PUBLICATIONS

U.S. Appl. No. 11/731,883, filed Mar. 30, 2007.

U.S. Appl. No. 11/731,873, filed Mar. 30, 2007.

U.S. Appl. No. 11/759,783, filed Jun. 7, 2007.

Collimator sheets found at the website: http://www.nuclearfields.com/indexproduct.htm.

* cited by examiner

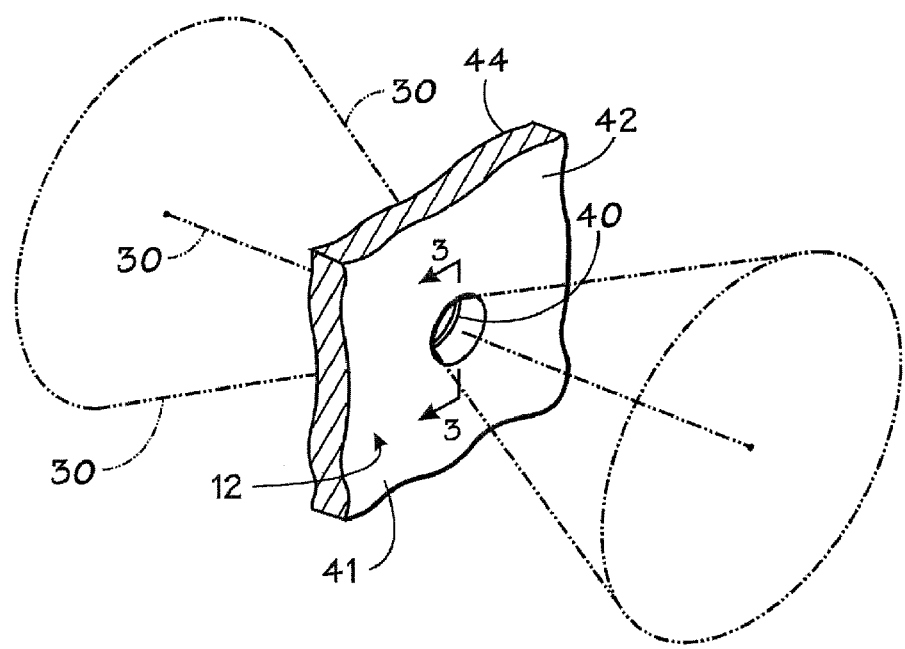
FIG. 2
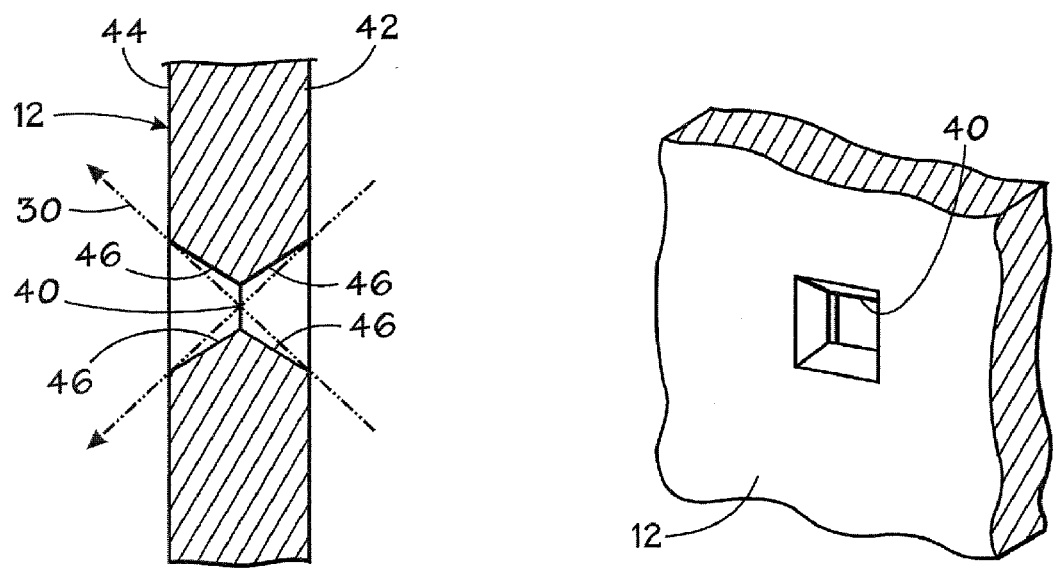
FIG. 3
FIG. 4

ADJUSTABLE-FOCAL-LENGTH COLLIMATORS METHOD AND SYSTEM

BACKGROUND

The invention relates generally to non-invasive imaging such as single photon emission computed tomography (SPECT) imaging. More particularly, the invention relates to imaging systems configured to have an adjustable focal length from a pinhole aperture in a collimator assembly to a detector assembly.

SPECT is used for a wide variety of imaging applications, such as medical imaging. In general, SPECT systems are imaging systems that are configured to generate an image based upon the impact of photons (generated by a nuclear decay event) against a gamma-ray detector. In medical and research contexts, these detected photons may be processed to formulate an image of organs or tissues beneath the skin.

To produce an image, one or more detector assemblies may be rotated around a subject. Detector assemblies are typically comprised of various structures working together to receive and process the incoming photons. For instance, the detector assembly may utilize a scintillator assembly (e.g., large sodium iodide scintillator plates) to convert the photons into visible light for detection by an optical sensor. This scintillator assembly may be coupled by a light guide to multiple photomultiplier tubes (PMTs) or other light sensors that convert the light from the scintillator assembly into an electric signal. In addition to the scintillator assembly-PMT combination, pixilated solid-state direct conversion detectors (e.g., CZT) may also be used to generate electric signals from the impact of the photons. This electric signal can be transferred, converted, and processed by electronic modules in a data acquisition module to facilitate viewing and manipulation by clinicians.

Typically, SPECT systems further include a collimator assembly that may be attached to the front of the gamma-ray detector. In general, the collimator assembly is designed to absorb photons such that only photons traveling in certain directions impact the detector assembly. In certain instances, pinhole-aperture collimators may be used. Pinhole-aperture collimators are generally collimators with one or more small pinhole apertures therein. Photons passing through these pinhole apertures generally project an inverted image of the source onto the detector assembly.

In general, the system resolution and sensitivity is at least partially based on the focal length (i.e., the distance from a pinhole aperture to the detector assembly). For example, the image may be magnified if the distance from the source to the pinhole aperture is less than the focal length from the pinhole aperture to the detector assembly. In a similar manner, the image may be minified if the distance from the source to the pinhole aperture is greater than the focal length from the pinhole aperture to the detector assembly. However, the distance to the source may vary for each pinhole aperture in the collimator assembly. By way of example, if a collimator assembly with multiple pinhole apertures is placed around a thorax to image a heart (which is generally eccentered anterior and left), the distance from each pinhole aperture to the heart will typically vary.

BRIEF DESCRIPTION

In accordance with one embodiment, the present technique provides an imaging system. The imaging system includes a collimator assembly having one or more apertures therein. The imaging system further includes a detector assembly configured to generate one or more signals in response to gamma rays that pass through the one or more apertures. The imaging system is configured so that at least one of the one or more apertures has an adjustable focal length.

In accordance with another embodiment, the present technique provides an imaging system. The imaging system includes one or more pinhole-detector modules. Each pinhole-detector module includes a collimator having one or more pinhole apertures therein. At least one of the pinhole-detector modules is configured so that at least one of the one or more pinhole apertures therein has an adjustable focal length. Each pinhole-detector module further includes a detector assembly configured to generate one or more signals in response to gamma rays that pass through the one or more pinhole apertures.

In accordance with another embodiment, the present technique provides a method of changing collimator performance. The method includes adjusting a focal length between a detector assembly and a pinhole aperture in a collimator assembly.

In accordance with another embodiment, the present technique provides a method of imaging a volume. The method includes positioning at least a portion of a subject in a field of view of a single photon emission computed tomography system. The method further includes collimating gamma rays emitted from the subject using one or more pinhole-detector modules. Each pinhole-detector module comprises a collimator having one or more pinhole apertures and a detector assembly. The method further includes detecting gamma rays that pass through the one or more pinhole apertures with the corresponding detector assembly. The method further includes generating one or more signals in response to the detected gamma rays. The method further includes adjusting a focal length for at least one of the pinhole-detector modules based on the one or more generated signals.

DRAWINGS

These and other features, aspects, and advantages of the present invention will become better understood when the following detailed description is read with reference to the accompanying drawings in which like characters represent like parts throughout the drawings, wherein:

FIGS. 2-4 are illustrations of a portion of a collimator assembly to illustrate a pinhole aperture in accordance with embodiments of the present technique;

DETAILED DESCRIPTION

Figure 1:
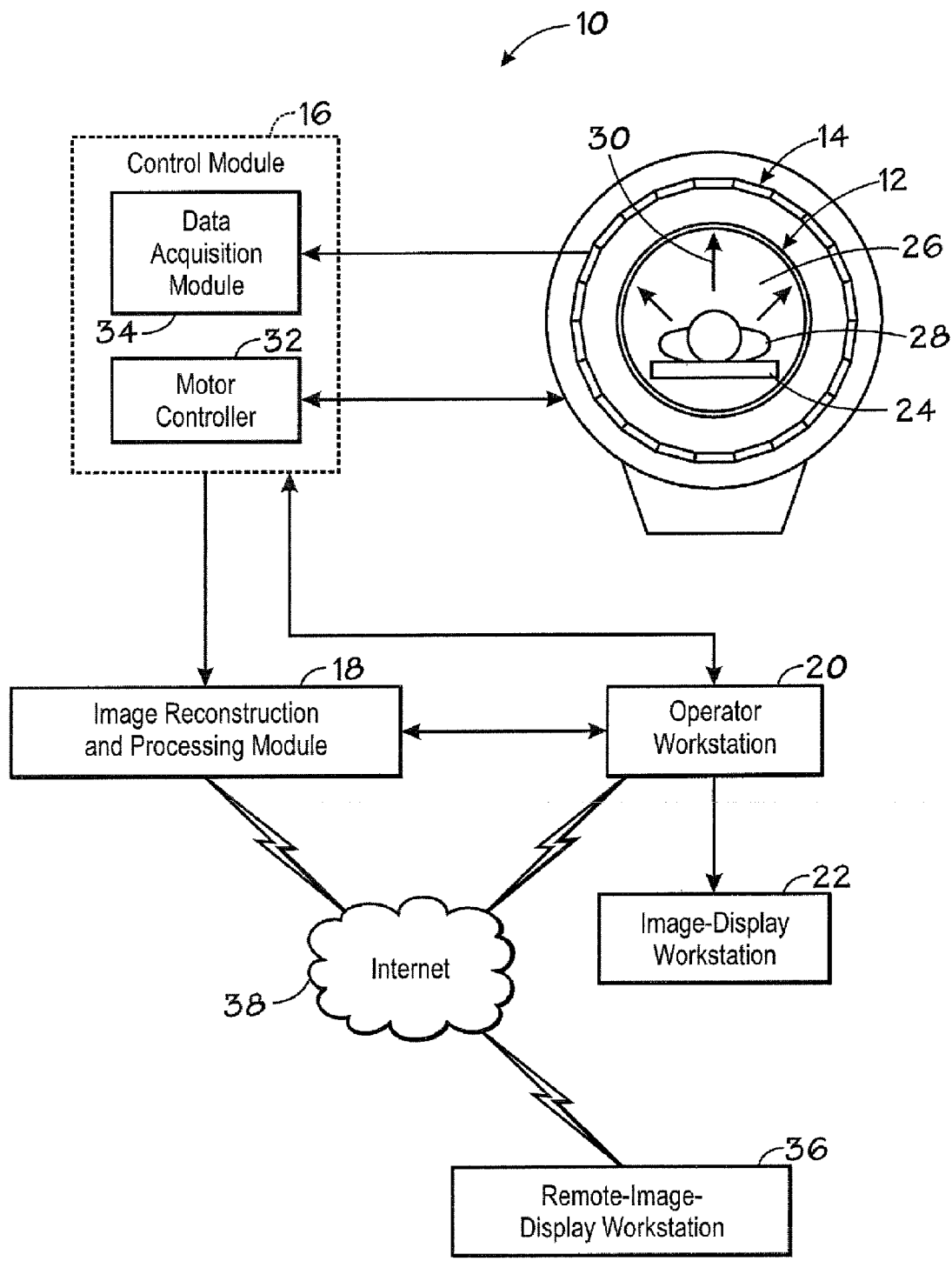
FIG. 1 is an illustration of an exemplary SPECT system which may include a collimator assembly having an adjustable focal length in accordance with embodiments of the present technique.

FIG. 1 illustrates an exemplary SPECT system 10 for acquiring and processing image data in accordance with exemplary embodiments of the present technique. As illustrated, the SPECT system 10 may include a collimator assembly 12 and a detector assembly 14. As will be discussed in more detail below, the focal length between one or more pinhole apertures in the collimator assembly 12 and the detector assembly 14 may be adjusted, for example, to modify system resolution and sensitivity. In the illustrated embodiment, the SPECT system 10 also includes a control module 16, an image reconstruction and processing module 18, an operator workstation 20, and an image-display workstation 22. Each of the aforementioned components will be discussed in greater detail in the sections that follow.

As illustrated, a subject support 24 (e.g. a table) may be moved into position in a field of view 26 of the SPECT system 10. In the illustrated embodiment, the subject support 24 is configured to support a subject 28 (e.g., a human patient, a small animal, a plant, a porous object, etc.) in a position for scanning. Alternatively, the subject support 24 may be stationary, while the SPECT system 10 may be moved into position around the subject 28 for scanning. Those of ordinary skill in the art will appreciate that the subject 28 may be supported in any suitable position for scanning. By way of example, the subject 28 may be supported in the field of view 26 in a generally vertical position, a generally horizontal position, or any other suitable position (e.g., inclined) for the desired scan. In SPECT imaging, the subject 28 is typically injected with a solution that contains a radioactive tracer. The solution is distributed and absorbed throughout the subject 28 in different degrees, depending on the tracer employed and, in the case of living subjects, the functioning of the organs and tissues. The radioactive tracer emits electromagnetic rays (e.g., photons or gamma quanta) known as "gamma rays" during a nuclear decay event, represented on FIG. 1 as gamma rays 30.

As previously mentioned, the SPECT system 10 includes collimator assembly 12 that collimates the gamma rays 30 emanating from the subject 28 positioned in the field of view 26. The collimator assembly 12 may be disposed between the detector assembly 14 and the field of view 26 and may contain a radiation-absorbent material, such as lead or tungsten, for example. In general, the collimator assembly 12 is configured to limit and define the direction and angular divergence of the gamma rays 30. In accordance with embodiments of the present technique, the collimator assembly 12 may include a pinhole collimator having one or more pinhole apertures therein. As will be discussed in more detail with respect to the following figures, the focal length (i.e., the length between a pinhole aperture and the detector assembly 14) of at least one of the pinhole apertures may be adjusted. In this manner, the system resolution and sensitivity may be modified without the need to swap an entire collimator assembly.

Referring again to FIG. 1, the collimator assembly 12 extends at least partially around the field of view 26. In exemplary embodiments, the collimator assembly 12 may extend up to about 360° around the field of view 26. By way of example, the collimator assembly 12 may extend from about 180° to about 360° around the field of view 26. In certain embodiments, the collimator assembly 12 may include one or more pinhole-collimator units positioned around the field of view 26, with each pinhole-collimator unit having one or more pinhole apertures therein.

The gamma rays 30 that pass through the pinhole apertures in the collimator assembly 12 impact the detector assembly 14. Due to the collimation of the gamma rays 30 by the collimator assembly 12, the detection of the gamma rays 30 may be used to determine the line of response along which each of the gamma rays 30 traveled before impacting the detector assembly 14, allowing localization of each gamma ray's origin to that line. In general, the detector assembly 14 may include a plurality of detector elements configured to detect the gamma rays 30 emanating from the subject 28 in the field of view 26 and passing through one or more pinhole apertures through the collimator assembly 12. In exemplary embodiments, each detector element produces an electrical signal in response to the impact of the gamma rays 30.

As will be appreciated by those of ordinary skill in the art, the detector elements of the detector assembly 14 may include any of a variety of suitable materials and/or circuits for detecting the impact of the gamma rays 30. By way of example, the detector elements may include a plurality of solid-state detector elements, which may be provided as one-dimensional or two-dimensional arrays. In another embodiment, the detector elements of the detector assembly 14 may include a scintillation assembly and PMTs or other light sensors.

Moreover, the detector elements may be arranged in the detector assembly 14 in any suitable manner. By way of example, the detector assembly 14 may extend at least partially around the field of view 26. In certain embodiments, the detector assembly 14 may include modular-detector elements arranged around the field of view 26. Alternatively, the detector assembly 14 may be arranged in a ring that may extend up to about 360° around the field of view 26. In certain exemplary embodiments, the detector assembly 14 may extend from about 180° to about 360° around the field of view 26. The ring of detector elements may include flat panels or curved detector surfaces (e.g., a NaI annulus). In one exemplary embodiment, the ring may comprise in the range from 9-10 solid-state detector panels with each detector panel comprising four detector modules. Those of ordinary skill in the art will appreciate that the ring need not be circular, for example, the detector elements may be arranged in an elliptical ring or be contoured to the body profile of the subject 28. In addition, in certain exemplary embodiments, the detector assembly 14 may be gimbaled on its support base, e.g., so that arbitrary slice angles may be acquired.

To acquire multiple lines of response emanating from the subject 28 in the field of view 26 during a scan, the collimator assembly 12 may be configured to rotate about the subject 28 positioned within the field of view 26. In accordance with exemplary embodiments, the collimator assembly 12 may be configured to rotate with respect to the detector assembly 14. By way of example, the detector assembly 14 may be stationary while the collimator assembly 12 may be configured to rotate about the field of view 26. Alternatively, the detector assembly 14 may rotate while the collimator assembly 12 is stationary. In certain exemplary embodiments, the collimator assembly 12 and the detector assembly 14 may both be configured to rotate, either together or independent of one another. Alternatively, if sufficient pinhole apertures are provided in the collimator assembly 12, then no rotation may be required.

As illustrated, SPECT system 10 further includes a control module 16. In the illustrated embodiment, the control module 16 includes one or more motor controllers 32 and a data-acquisition module 34. In general, the motor controller 32 may control the rotational speed and position of the detector assembly 14, the collimator assembly 12, and/or the position of the subject support 24. In addition, the motor controllers 32 may control orientation of individual detectors 14 which may move independently or in combination with sections of the collimator assembly 12. Further, the motor controllers 32 may operate actuators to change separation between the detector assembly 14 and the collimator assembly 12, therefore changing focal length. The data-acquisition module 34 may be configured to obtain the signals generated in response to the impact of the gamma rays 30 with the detector assembly 14. For example, the data-acquisition module 34 may receive sampled electrical signals from the detector assembly 14 and convert the data to digital signals for subsequent processing by the image reconstruction and processing module 18.

Those of ordinary skill in the art will appreciate that any suitable technique for data acquisition may be used with the SPECT system 10. By way of example, the data needed for image reconstruction may be acquired in a list or a frame mode. In one exemplary embodiment of the present technique, gamma ray events (e.g., the impact of gamma rays 30 on the detector assembly 14), gantry 16 motion (e.g., collimator assembly 12 motion, detector assembly 14 position, and subject support 24 position), and physiological signals (e.g., heart beat and respiration) may be acquired in a list mode. List mode may be suitable in exemplary embodiments where the count rate is relatively low and many pixels record no counts at each gantry position or physiological gate. Alternatively, frames and physiological gates may be acquired by moving the gantry in a step-and-shoot manner and storing the number of events in each pixel during each frame time and heart or respiration cycle phase. Frame mode may be suitable, for example, where the count rate is relatively high and most pixels are recording counts at each gantry position or physiological gate.

In the illustrated embodiment, the image reconstruction and processing module 18 is coupled to the data-acquisition module 34. The signals acquired by the data-acquisition module 34 may be provided to the image reconstruction and processing module 18 for image reconstruction. The image reconstruction and processing module 18 may include electronic circuitry to receive acquired signals, and electronic circuitry to condition the acquired signals received from the data-acquisition module 34. Further, the image reconstruction and processing module 18 may include processing to coordinate functions of the SPECT system 10 and implement reconstruction algorithms suitable for reconstruction of the acquired signals. The image reconstruction and processing module 18 may include a digital-signal processor, memory, a central-processing unit (CPU) or the like, for processing the acquired signals. As will be appreciated, the processing may include the use of one or more computers. The addition of a separate CPU may provide additional functions for image reconstruction, including, but not limited to, signal processing of data received, and transmission of data to the operator workstation 20 and image display workstation 22. In one embodiment, the CPU may be confined within the image reconstruction and processing module 18, while in another embodiment a CPU may include a stand-alone device that is separate from the image reconstruction and processing module 18.

The reconstructed image may be provided to the operator workstation 20. The operator workstation 20 may be utilized by a system operator to provide control instructions to some or all of the described components and for configuring the various operating parameters that aid in data acquisition and image generation. An image display workstation 22 coupled to the operator workstation 20 may be utilized to observe the reconstructed image. It should be further noted that the operator workstation 20 and the image-display workstation 22 may be coupled to other output devices, which may include printers and standard or special purpose computer monitors. In general, displays, printers, workstations and similar devices supplied with the SPECT system 10 may be local to the data-acquisition components, or may be remote from these components, such as elsewhere within the institution or hospital, or in an entirely different location, linked to the image acquisition system via one or more configurable networks, such as the Internet, virtual private networks, and so forth. By way of example, the operator workstation 20 and/or the image reconstruction and processing module 18 may be coupled to a remote-image display workstation 36 via a network (represented on FIG. 1 as Internet 38).

Furthermore, those of ordinary skill in the art will appreciate that any suitable technique for image reconstruction may be used with the SPECT system 10. In one exemplary embodiment, iterative reconstruction (e.g., ordered subsets expectation maximization, OSEM) may be used. Iterative reconstruction may be suitable for certain implementations of the SPECT system 10 due, for example, to its speed and the ability to tradeoff reconstruction resolution and noise by varying the convergence and number of iterations.

While in the illustrated embodiment, the control module 16 (including the data-acquisition module 34 and the motor controller 32) and the image reconstruction and processing module 18 are shown as being outside the detector assembly 14 and the operator workstation 20. In certain other implementations, some or all of these components may be provided as part of the detector assembly 14, the operator workstation 20, and/or other components of the SPECT system 10.

Referring now to FIGS. 2 and 3, a view of one pinhole aperture 40 through the collimator assembly 12 is illustrated. Only a portion of the collimator assembly 12 is shown to illustrate how gamma rays pass through the pinhole aperture 40. As illustrated by FIGS. 2 and 3, pinhole aperture 40 opens on both sides in the shape of a cone: from the interior surface 42 toward the field of view 26 and from the exterior surface 44 toward the detector assembly 14. With this arrangement, gamma rays traveling in a direction oblique to the pinhole aperture 40 may pass through the collimator assembly 12. Accordingly, gamma rays that pass through the pinhole aperture 40 would have a cone-beam geometry, as indicated by gamma rays 30. Gamma rays that do not pass through the pinhole aperture 40 would be at least substantially absorbed by the collimator assembly 12. In the illustrated embodiment, the pinhole aperture 40 is defined by angled segments 46 of the collimator assembly 12. Those of ordinary skill in the art will appreciate that varying the angle of the angled segments 46 should affect, for example, the field of view of the pinhole aperture 40, the extent of potential overlap of the projected pinhole cone beams on the detector assembly 14, the sensitivity of the pinhole aperture 40, and the proportion of gamma rays that penetrate the edges of the collimator assembly 12 surrounding the pinhole aperture 40.

As illustrated by FIG. 2, the one or more pinhole apertures (such as pinhole aperture 40) through the collimator assembly 12 may have a substantially circular configuration. Other aperture configurations, however, may also be suitable. By way of example, the collimator assembly 12 may be configured as having aperture configurations that are substantially polygonal (e.g., three-sided, four-sided, five-sided, six-sided, and so forth), or substantially curved (e.g., elliptical, circular, and so forth). By way of example, FIG. 4 illustrates a perspective view of a pinhole aperture 40 through the collimator assembly 12 having a substantially polygonal configuration and specifically having a substantially square configuration. Those of ordinary skill in the art will appreciate that the pinhole configuration may be selected based on the desired resolution, sensitivity, field of view, and so forth, including consideration of the performance of the image reconstruction and processing module 18. Further, those of ordinary skill in the art will appreciate that varying the aperture configuration will generally impact the resolution, sensitivity, and field of view of the SPECT system 10. In certain embodiments, one or more of the pinhole apertures 40 may have an adjustable aperture to allow selection of various points along the sensitivity-versus-resolution curve during the same scan without removal of the subject from the field of view 26. Additionally, the portion of the collimator assembly 12 surrounding the pinhole aperture 40 may be constructed from the same or different material as that used for the remainder of the photon-absorbing collimator assembly 12.

Furthermore, as illustrated by FIG. 3, the one or more pinhole apertures (such as pinhole aperture 40) through the collimator assembly 12 may have pinhole-aperture edges that are sharp. As illustrated, the angled sections 46 define a pinhole aperture 40 having a knife-edge configuration. Those of ordinary skill in the art will appreciate that varying the pinhole-aperture-edge configuration will generally impact the resolution, sensitivity, and field of view of the SPECT system 10. In exemplary embodiments, the collimator assembly 12 may be configured as having pinhole-aperture edges that are sharp (e.g., knife edge as in FIG. 3) or blunted (e.g., keel edge or round edge). Other pinhole-aperture-edge configurations may also be suitable. Those of ordinary skill in the art will appreciate that the pinhole-aperture-edge configuration may be selected based on the desired resolution, sensitivity, field of view, and so forth, including consideration of the performance of the image reconstruction and processing module 18.

Figure 7:
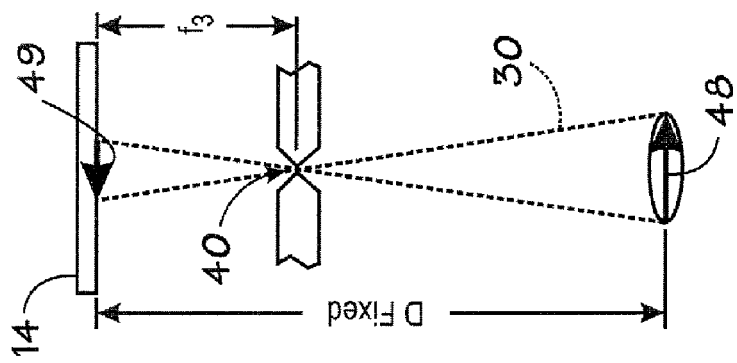
FIGS. 5-16 illustrate adjustment of a focal length between a pinhole aperture and a detector assembly in accordance with embodiments of the present technique.
Figure 6:
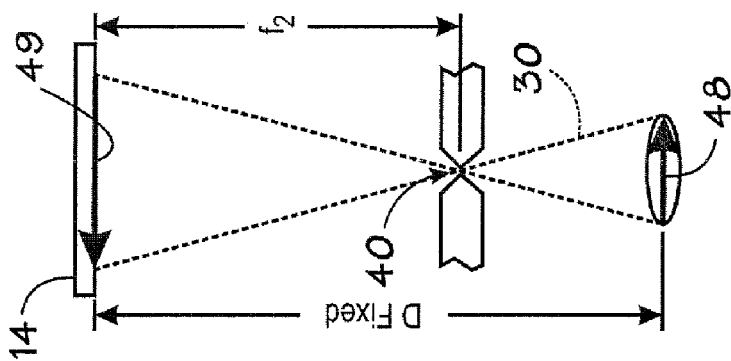
Figure 5:
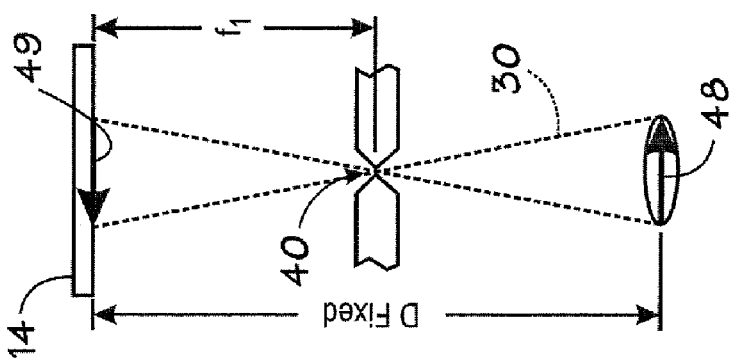

Referring now to FIGS. 5-7, adjustment of the focal length between the pinhole aperture 40 and the detector assembly 14 is illustrated, in accordance with one embodiment of the present technique. In FIG. 5, the focal length between the pinhole aperture 40 and the detector assembly 14 is represented by the reference character $f_1$. As illustrated in FIGS. 5-7, the focal length between the pinhole aperture 40 and the detector assembly 14 may be increased from $f_1$ to $f_2$ or may be decreased from $f_1$ to $f_3$. As will be appreciated, increasing (or decreasing) the focal length should generally result in a corresponding increase (or decrease) in the size of the projection 49 of the object 48 onto the detector assembly 14. As illustrated in FIG. 5, there is no magnification of the object 48 and the projection 49 of the object 48 is reverse in orientation. As illustrated in FIG. 6, increasing the focal length should result in a corresponding enlargement (magnification) of the source's projection 49 as the pinhole aperture 40 moves farther away from the detector assembly 14. As illustrated in FIG. 7, reducing the focal length resulted in a corresponding reduction (minification) of the source's projection 49 as the pinhole aperture 40 moves closer to the detector assembly 14. It should be noted that, for this example, the object length between the source 48 emanating the gamma rays 30 and the detector assembly 14 is fixed and represented as $D_{fixed}$. Other embodiments of this invention that include variable object length are discussed below.

As will be appreciated, to adjust the focal length the pinhole aperture 40 and the detector assembly 14 may be moved with respect to one another. For example, to decrease the focal length, the detector assembly 14 may be moved closer to the pinhole aperture 40 or vice versa. In a similar manner, to increase the focal length, the detector assembly 14 may be moved further away from the pinhole aperture 40 or vice versa. While the preceding discussion describes movement of either the detector assembly 14 or the pinhole aperture 40 to adjust the focal length, those of ordinary skill in the art will appreciate that movement of both the detector assembly 14 and the pinhole aperture 40 may be employed for focal-length adjustment.

As previously mentioned, the focal length between one or more pinhole apertures in the collimator assembly 12 and the detector assembly 14 may be adjusted, for example, to modify system resolution and sensitivity. In contrast, conventional imaging systems are typically designed to have a fixed focal length for a particular collimator assembly, wherein focal-length adjustment may not be effected without a time-consuming collimator exchange. However, in accordance with embodiments of the present technique, the focal length between a particular collimator assembly 12 and the detector assembly 14 may be adjusted without the need for collimator exchange. Indeed, in accordance with exemplary embodiments, the focal length may be individually or collectively adjusted for each pinhole aperture in the collimator assembly 12. In exemplary embodiments, focal length may be changed to provide substantially the same image magnification (or minification) for each pinhole aperture. Moreover, in exemplary embodiments, the focal length may be changed to maximize the use of detector area for each pinhole aperture. As will be appreciated, increasing focal length generally should increase system resolution if there is no change in the distance between the source 48 and the pinhole aperture 40. Conversely, decreasing focal length generally should decrease system resolution if there is no change in the distance between the source 48 and the pinhole aperture 40.

Figure 10:
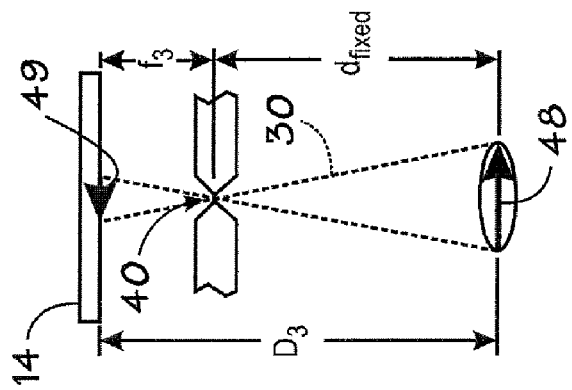
Figure 9:
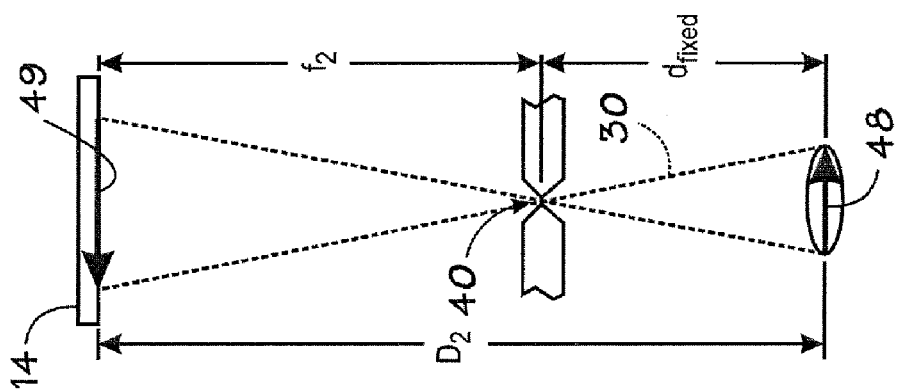
Figure 8:
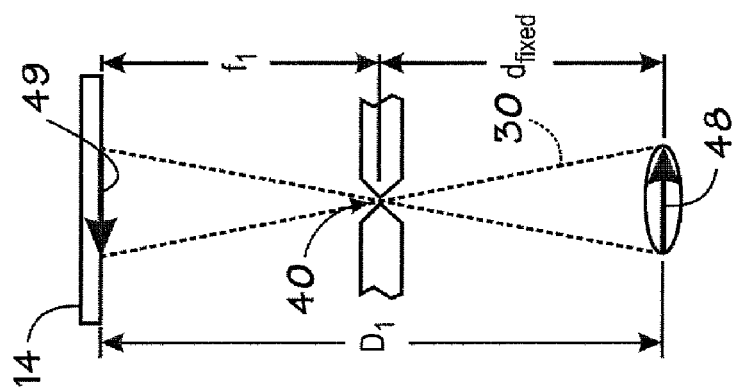

FIGS. 8-16 describe three additional examples for adjustment of the focal length between the pinhole aperture 40 and the detector assembly 14. As illustrated in FIGS. 8-10, the focal length between the pinhole aperture 40 and the detector assembly 14 may be increased from $f_1$ to $f_2$ or may be decreased from $f_1$ to $f_3$ without changing the distance $d_{fixed}$ from the object 48 to the pinhole aperture 40. As previously discussed, increasing (or decreasing) the focal length should generally result in a corresponding increase (or decrease) in the size of the projection 49 of the source 48 onto detector 14. FIG. 8 illustrates no magnification of the object 48 with the projection 49 of the object 48 reverse in orientation. FIG. 9 illustrates the projection 49 of the object 48 magnified (e.g., 2×) as the detector assembly 14 moves away from the pinhole aperture 40. FIG. 10 illustrates the projection 49 of the object 48 minified (e.g, ½×) in the plane of the detector assembly 14 as the detector assembly 14 moves to the pinhole aperture 40.

In the illustrated embodiment, the object length from the object 48 to the detector assembly 14 varies when the focal length is adjusted. As illustrated, the object length increases from $D_1$ to $D_2$ when the focal length increases from $f_1$ to $f_2$, and the object length decreases from $D_1$ to $D_3$ when the focal length decreases from $f_1$ to $f_3$. Because the difference between the object length and the focal length does not vary ($D_1-f_1=D_2-f_2=D_3-f_3$), the distance $d_{fixed}$ from the object 48 to the pinhole aperture 40 remains fixed. Therefore, the sensitivity remains constant even though image resolution changes. As will be appreciated, changing image resolution without changing sensitivity may be used, for example, to scout a region of interest, and then focus on a smaller feature in the region of interest with a higher resolution. For example, this may be useful in clinical screening of possible cancer metastasis.

Figure 13:
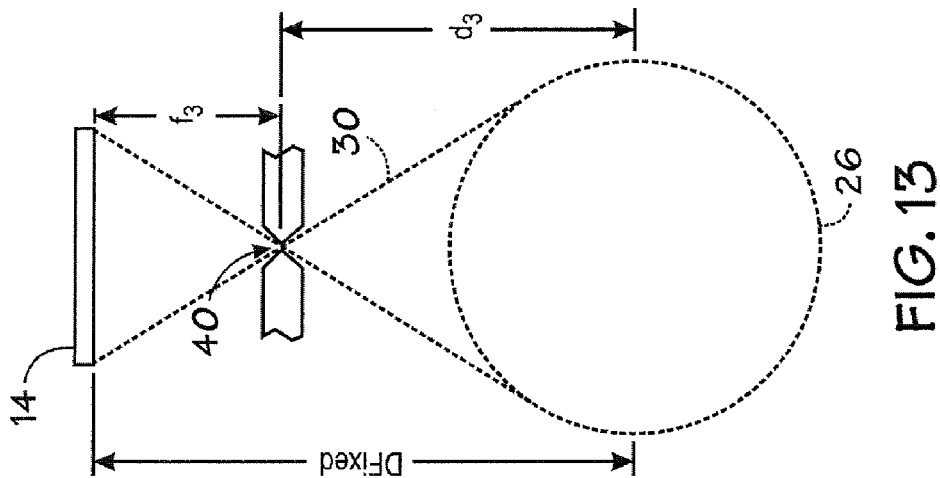
Figure 12:
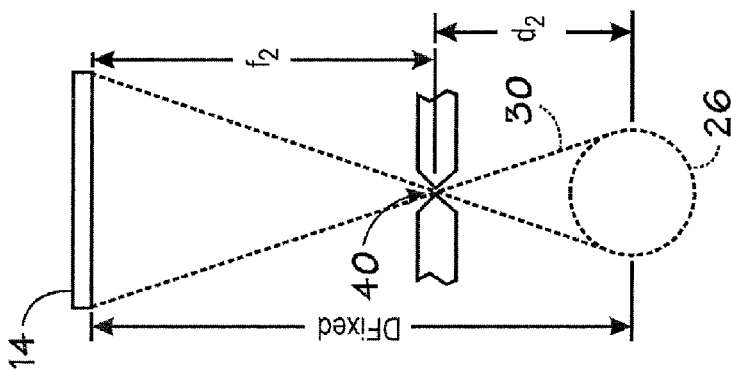
Figure 11:
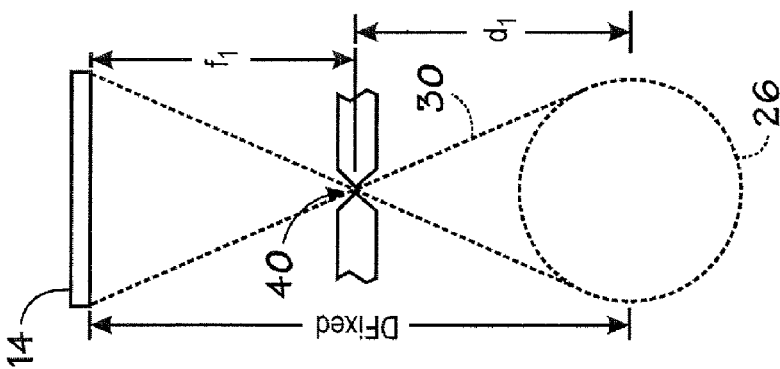

As illustrated in FIGS. 11-13, the focal length may be adjusted to change the size of the field of view 26. In the illustrated embodiment, three different field of view 26 sizes are shown that correspond to three different focal length $f_1$, $f_2$, and $f_3$ while the object length $D_{fixed}$ from the center of the field of view 26 to the detector assembly 14 is fixed. FIG. 11 illustrates no magnification of an object in the field of view 26 for a focal length of $f_1$. FIG. 12 illustrates magnification (e.g., 2×) of an object in the field of view 26 for a focal length of $f_2$. FIG. 13 illustrates minification (e.g, ½×) for a focal length of $f_3$. Because the difference between the object length and the focal length varies, the distance from the center of the field of view 26 to the pinhole aperture 40 changes as the focal length is adjusted. As illustrated, the distance from the center of the field of view 26 to the pinhole aperture 40 decreases from $d_1$ to $d_2$ when the focal length is increased from $f_1$ to $f_2$, and the distance increases from $d_1$ to $d_3$ when the focal length is decreased from $f_1$ to $f_3$. Accordingly, the sensitivity increases and the size of the field of view 26 decreases as the distance from the center of the field of view 26 to the pinhole aperture 40 decreases, and the sensitivity decreases and the size of the field of view 26 increases as the distance from the center of the field of view 26 to the pinhole aperture 40 increases. The embodiment illustrated in FIGS. 11-13 may incorporated, for example, into an imaging system with a fixed detector assembly 14 on a gantry capable of scouting a larger region of interest with lower resolution and sensitive, then focusing on a smaller region with higher resolution and sensitivity.

Figure 16:
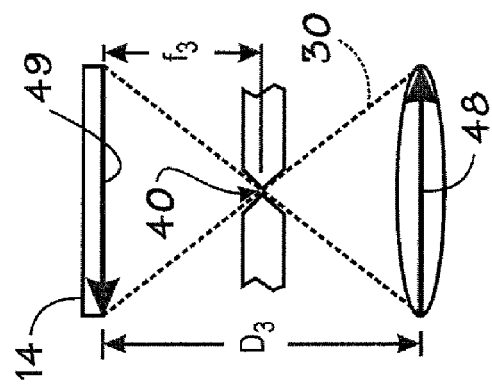
Figure 15:
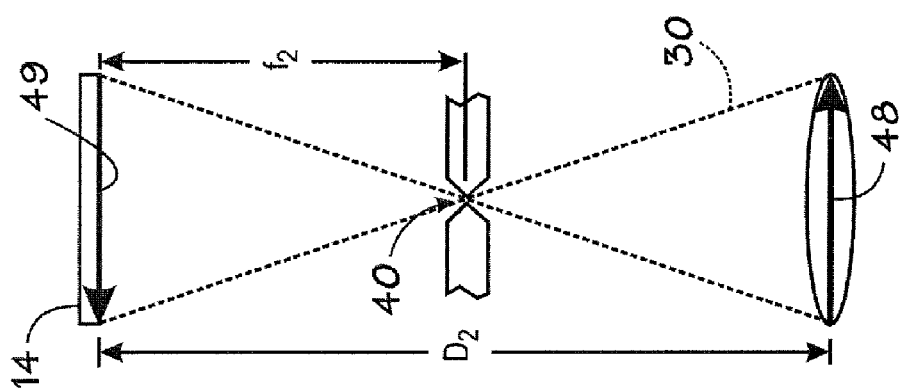
Figure 14:
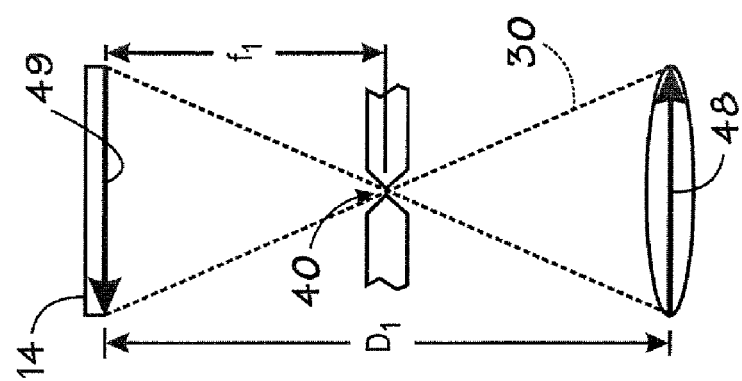

As illustrated in FIGS. 14-16, the focal length may be adjusted to maximize usage of the detector assembly 14 when the object length from the detector assembly 14 to the object 48 is changed. By way of example, the focal length may be adjusted to create a projection 49 that maximizes the available sensitive area of detector assembly 14. FIGS. 14-16 illustrate three different object lengths $D_1$, $D_2$, and $D_3$ from the object 48 to the detector assembly 14. As illustrated, the focal length may be adjusted such that the projection 49 of the object 48 extends to fit the available detector assembly 14. FIG. 14 illustrates a projection 49 of the object 48 that fully utilizes the detector assembly for a focal length of $f_1$. FIGS. 15 and 16 illustrate focal lengths of $f_2$ and $f_3$ that have been adjusted larger and shorter, respectively, such that the projection 49 of the object 48 also fully utilizes the detector assembly 14.

Advantageously, exemplary embodiments of the present technique may be employed to adjust focal length between one or more pinhole apertures and the detector assembly 14 during an examination. For example, it may be desired to individually adjust the focal length with the subject 28 positioned in the imaging system 10. In one exemplary embodiment, the focal length may be adjusted to provide substantially the same image magnification (or minification) for each pinhole aperture. By way of example, it may be desired to image the subject's heart. As will be appreciated, the subject's heart will generally not be centered in the field of view as it is typically eccentered and anterior. Accordingly, the distance from the subject's heart to each pinhole aperture in the collimator assembly 12 will vary. If the focal length is the same for each pinhole aperture this will result in different magnification (or minification) for each pinhole aperture. It may be desired, however, to image the heart with the substantially the same magnification (or minification) for each pinhole aperture. In accordance with an embodiment of the present technique, the focal length between one or more pinhole apertures and the detector assembly 14 may be adjusted so that the heart may be imaged with substantially the same magnification (or minification) for each pinhole aperture.

Figure 17:
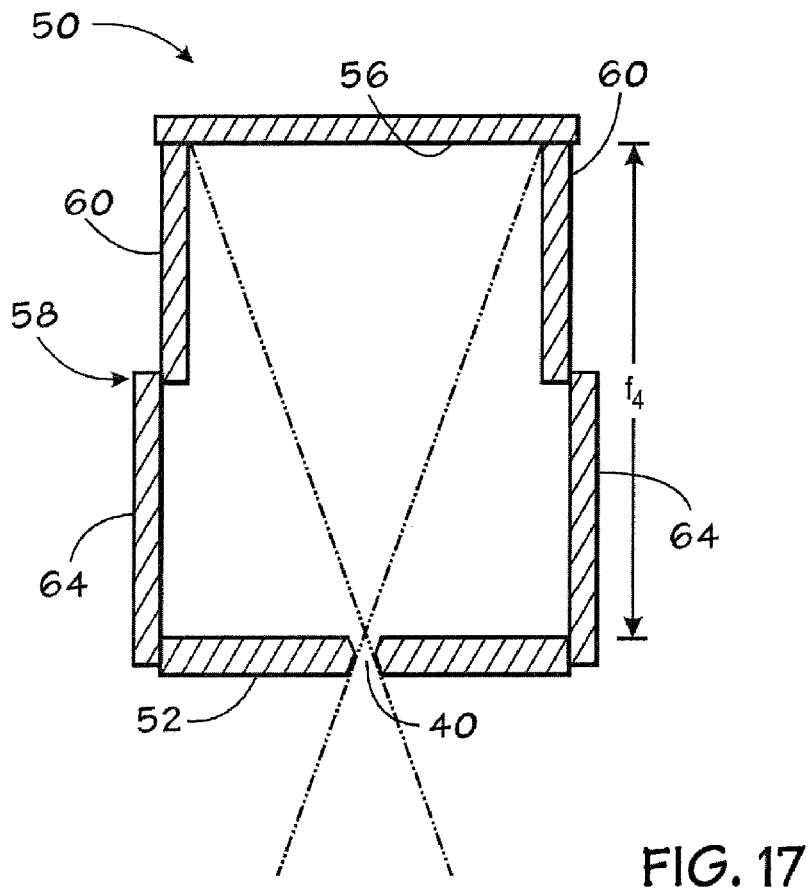
FIGS. 17-18 are cross-sectional views of an exemplary pinhole-detector module configured to have an adjustable focal length in accordance with embodiments of the present technique.
Figure 18:
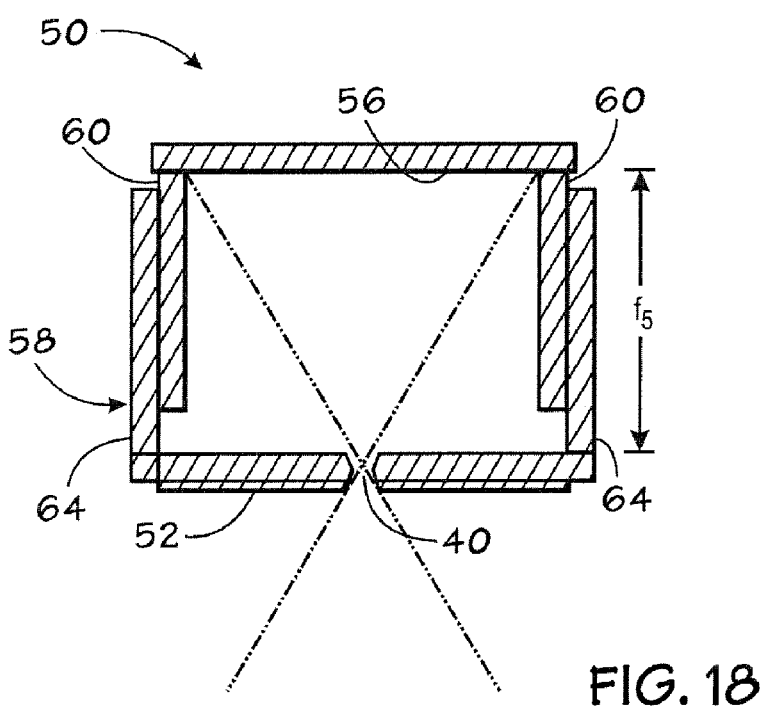

FIGS. 17 and 18 illustrate one technique for implementing a pinhole aperture with an adjustable focal length, in accordance with an embodiment of the present technique. In the exemplary embodiment, a pinhole-detector module 50 is illustrated that includes a pinhole collimator 52 having at least one pinhole aperture 40 therein and a detector panel 56. As illustrated, the pinhole collimator 52 and the detector panel 56 may be interconnected by a collapsible assembly 58. By way of example, the collapsible assembly 58 may be a bellows-type assembly. In accordance with exemplary embodiments, the collapsible assembly 58 may be configured to adjust the focal length between the pinhole aperture 40 and the detector panel 56.

In one exemplary embodiment, the collapsible assembly 58 includes a plurality of sections (e.g., panels) that are collapsible to adjust the focal length between the detector panel 56 and the pinhole aperture 40. As illustrated, the collapsible assembly 58 may include top panels 60 that may each be coupled to the detector panel 56. Further, the collapsible assembly 58 may include bottom panels 64 that may each be coupled to the pinhole collimator 52. The top panels 60 and bottom panels 64 may each contain a gamma-ray absorbent material to shield the detector from gamma rays that do not pass through the pinhole aperture 40. Further, either the top panels 60 or the bottom panels 64 should be configured to move in the direction to change the focal length $f_4$ so as to collapse (or extend) the pinhole-detector module 50 and, thus, effect focal-length adjustment. By way of example, the bottom panels 64 may be slidably connected to the top panels 60 so as to collapse (or extend) the pinhole-detector module dependent on the direction of movement. As illustrated in FIG. 17, when the collapsible assembly 50 is fully extended the detector panel 56 and a pinhole aperture 40 have a maximum focal length of $f_4$. As will be appreciated, the focal length may be decreased from a maximum focal length of $f_4$ to a decreased focal length of $f_5$ by collapsing the top panels 60 and the bottom panels 64, as illustrated in FIGS. 17 and 18.

In the exemplary embodiment illustrated in FIGS. 17 and 18, the detector panel 56 may include one or more solid-state detector elements, which may be provided as one-dimensional or two-dimensional arrays. As will be appreciated, while a flat detector panel is illustrated, any of a number of other suitable detector assemblies may be utilized in the pinhole-detector module, such as a scintillation assembly and PMTs or other light sensors. As will be appreciated, curved detectors may also be utilized.

Figure 19:
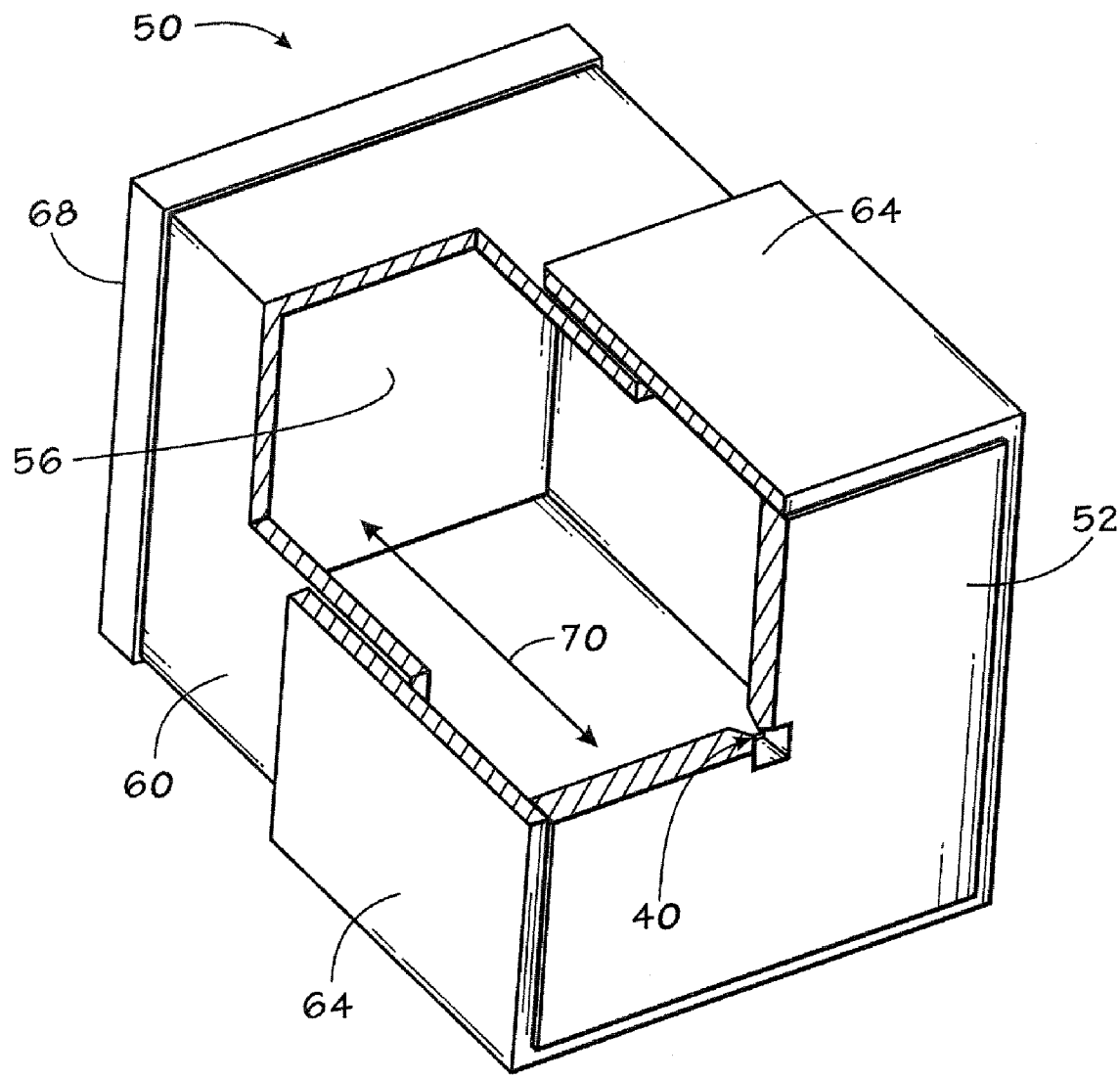
FIG. 19 is a prospective, cut-away view of a pinhole-detector module similar to the modules of FIGS. 17-18 to illustrate the adjustable focal length in accordance with embodiments of the present technique.

Referring now to FIG. 19, a cut-away view of the pinhole-detector module 50 is illustrated, in accordance with one embodiment of the present technique. Generally, the pinhole-detector module 50 may include the pinhole collimator 52 having at least one pinhole aperture 40 therein and the detector panel 56, wherein the focal length from the pinhole aperture 40 to the detector panel 56 is adjustable. As illustrated, the pinhole-detector module 50 further includes bottom panels 64 coupled to the pinhole collimator 52. The bottom panels 64 may be slidably coupled to the top panels 60. As illustrated, the top panels 60 may be coupled to an end plate 68 of the pinhole-detector module 50. The detector panel 56 may be mounted on an inner surface (not shown) of the end plate 68. As previously discussed, the pinhole-detector module 50 may be configured so that movement of at least one of the pinhole collimator 52 or the detector panel 56 in the direction 70 should adjust the focal length.

Figure 20:
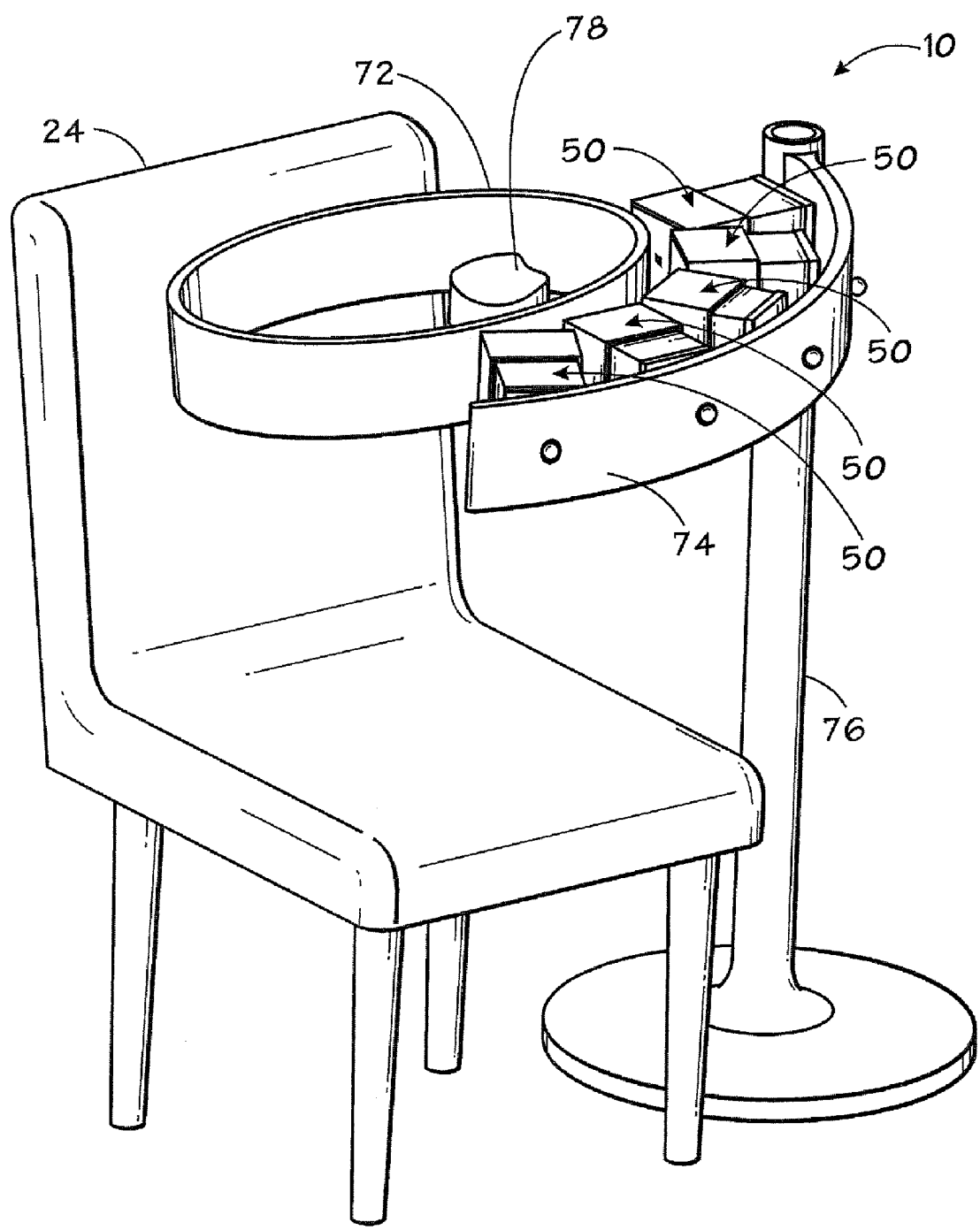
FIGS. 20-21 illustrate a plurality of pinhole-detector modules similar to the pinhole-detector module of FIGS. 17-19 and arranged about a patient cross-section.

As will be appreciated, an exemplary imaging system 10 may include a plurality of the pinhole-detector modules 50 that may be arranged at least partially around a subject. FIG. 20 illustrates an imaging system 10 that includes a plurality of detector modules 50 arranged at least partially around a subject (illustrated as subject cross section 72) in accordance with one embodiment of the present technique. As will be described in more detail below, the focal length between the pinhole aperture and detector assembly in each pinhole-detector module 50 may be individually adjustable. Also illustrated in FIG. 20 are support arm 74, support base 76, target organ 78 and subject support 24, as will be appreciated by those of ordinary skill in the art. While not illustrated in FIG. 20, each pinhole-detector module 50 may be coupled (e.g., via a wired or wireless connection) to one or more additional components of an imaging system, such as a control module, image reconstruction and processing module, operator workstation, image display workstation, and/or remote image display workstation as described above with respect to FIG. 1.

As illustrated in FIG. 20, the pinhole-detector modules 50 may be arranged on a plane generally perpendicular to the longitudinal axis of the subject cross section 72. As illustrated, the pinhole-detector modules 50 may be arranged in a generally arc-shaped configuration. In the illustrated embodiment, each pinhole-detector module 50 is coupled to support arm 74 that supports the pinhole-detector module 50 in a desired position for imaging. As will be appreciated, the support arm 74 may be of any suitable shape and/or design for supporting the pinhole-detector modules 50 in a desired position for scanning. For example, the support arm 74 is illustrated as a generally arc-shaped arm that supports the pinhole-detector modules 50 in a generally horizontal position. In the illustrated embodiment, the support arm 74 is coupled to support base 76. In general, the support base 76 supports the support arm 74 in a generally horizontal position. While the embodiment illustrated in FIG. 20 depicts the support arm 74 supporting the pinhole-detector modules 50 in a generally horizontal position, and the subject support 24 supporting the subject in a generally vertical position, other suitable configurations are encompassed within the present technique. By way of example, the subject support 24 may support the subject in a generally horizontal or otherwise reclined position while the support arm 74 may support the pinhole-detector modules 50 in a plane perpendicular or oblique to the longitudinal axis of the subject.

Figure 21:
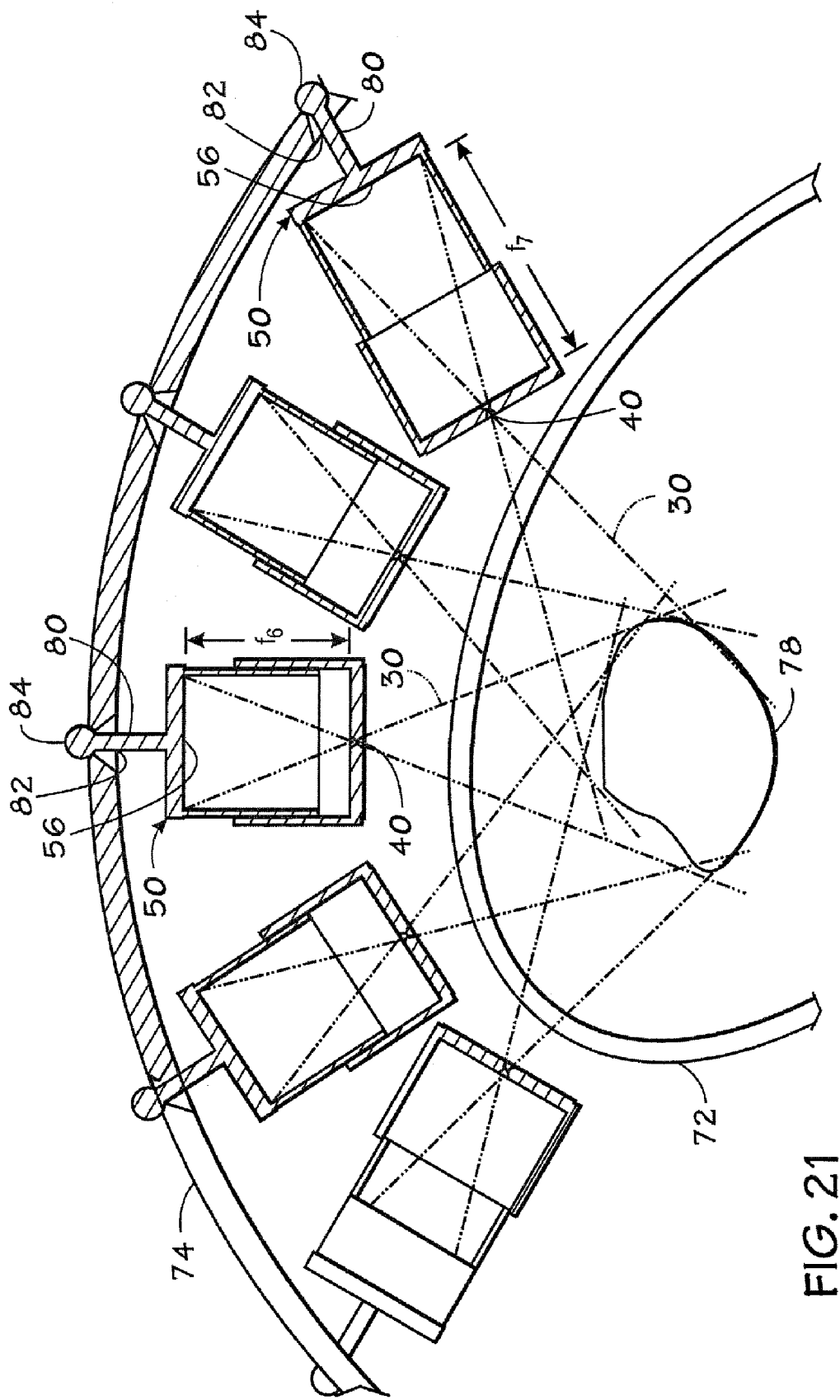

In accordance with exemplary embodiments of the present technique, the focal length between one or more pinhole apertures 40 and the detector assembly 56 in each pinhole-detector module 50 may be adjustable. Referring now to FIG. 21, a cross-sectional view of the pinhole-detector modules 50 and support arm 74 is provided to illustrate the adjustable focal length. As illustrated in FIG. 21, each pinhole-detector module 50 may include at least one pinhole aperture 40 and the detector panel 56. Each pinhole-detector module 50 may be configured to have an adjustable focal length between the pinhole aperture 40 and the detector panel 56. As illustrated, one of the pinhole-detector modules 50 may be adjusted to have a focal length of $f_6$ while another of the pinhole-detector modules 50 may also be adjusted to have a focal length of $f_7$. The focal lengths of the other pinhole-detector modules 50 may be adjusted as desired for a particular application. For example, the focal lengths may be changed to provide substantially the same image magnification (or minification) for each pinhole aperture 40 in the pinhole-detector modules 50. Additionally, the focal length may be changed to maximize the use of detector area for each pinhole aperture 40.

Also illustrated in FIG. 21 is the connection between the pinhole-detector modules 50 and the support arm 74. In exemplary embodiments, the pinhole-detector modules 50 may be moveably coupled to the support arm 74. By way of example, one or more of the pinhole-detector modules 50 may be coupled to the support arm 74 in a manner that allows the position and/or orientation of the pinhole-detector module 50 with respect to the patient cross-section 72 to be adjusted. In the illustrated embodiment, the pinhole-detector modules 50 are pivotally coupled to the support arm 74. As illustrated, each pinhole detector module 50 may include a connection arm 80 that extends through a corresponding opening 82 in the support arm 74. A ball 84 that is larger than the corresponding opening 82 may be located at the end of the connection arm 80 to connect each pinhole-detector module 50 to the support arm 74. As will be appreciated, a variety of other techniques may be suitable for connecting the pinhole-detector modules 50 to the support arm 74.

While the preceding discussion has described collimators with an adjustable focal length, one or more of the pinhole-detector modules 50 may be configured to have an adjustable orientation with respect to the subject 28 in accordance with exemplary embodiments of the present technique. The orientation of each pinhole-detector module may be adjusted based, for example, on the desired portion of the subject 28 to be imaged. This may be desirable, for example, when imaging a patient's heart that is not centered with respect to each pinhole-detector module 50. As illustrated in FIG. 21, each of the pinhole-detector modules 50 has an adjustable orientation with respect to the patient cross-section 72. Accordingly, the orientation of each pinhole-detector module 50 may be adjusted so that the field of view (represented on FIG. 21 by gamma rays 30) includes the target organ 78.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging system, comprising:
   a collimator assembly having a plurality of apertures therein; and
   a detector assembly configured to generate one or more signals in response to gamma rays that pass through the one or more apertures;
   wherein the imaging system is configured so that two or more of the plurality of the apertures have an independently adjustable focal length.

2. The imaging system of claim 1, wherein the collimator assembly is configured to move with respect to the detector assembly.

3. The imaging system of claim 1, wherein the detector assembly is configured to move with respect to the collimator assembly.

4. The imaging system of claim 1, comprising a means for adjusting the focal length of the at least one of the one or more pinhole apertures.

5. The imaging system of claim 1, wherein the one or more apertures include pinhole apertures having a substantially polygonal or a substantially curved configuration.

6. The imaging system of claim 1, wherein at least one of the one or more apertures has an adjustable aperture size.

7. The imaging system of claim 1, comprising:
   a module configured to receive the one or more signals and to process the one or more signals to generate one or more images;
   an image display workstation configured to display the one or more images; and
   a subject support for supporting a subject in a field of view of the imaging system.

8. An imaging system, comprising:
   a plurality of pinhole-detector modules arranged about a volume, each pinhole-detector module comprising:
     a collimator having one or more pinhole apertures therein, wherein two or more of the pinhole-detector modules are configured so that at least one of the one or more pinhole apertures therein has an independently adjustable focal length; and a detector assembly configured to generate one or more signals in response to gamma rays that pass through the one or more pinhole apertures.

9. The imaging system of claim 8, comprising a support arm coupled to each pinhole-detector module, wherein the support arm is configured to support the pinhole-detector modules in position around an imaging field of view.

10. The imaging system of claim 9, wherein at least one of the pinhole detector modules is movably coupled to the support arm.

11. The imaging system of claim 9, wherein at least one of the pinhole detector modules is pivotally coupled to the support arm.

12. The imaging system of claim 8, wherein at least one of the pinhole-detector modules is configured to have an adjustable orientation with respect to the volume.

13. The imaging system of claim 8, comprising a means for adjusting the focal length of the at least one of the one or more pinhole apertures.

14. The imaging system of claim 8, wherein each pinhole detector module comprises a plurality of radiation-absorbent panels interconnecting the collimator and the detector assembly.

15. A method of changing collimator performance, comprising:

independently adjusting focal lengths between a detector assembly and a plurality of pinhole apertures in a collimator assembly.

16. The method of claim 15, wherein the focal length is adjusted based on image magnification and/or minification.

17. The method of claim 15, wherein the focal length is adjusted based on use of detector area for the pinhole apertures.

18. The method of claim 15, wherein the focal length is adjusted based on size of an image field of view.

19. The method of claim 15, wherein the focal length is adjusted based on image resolution.

20. The method of claim 15, wherein the adjusting the focal length comprises moving the detector assembly with respect to the pinhole aperture.

21. The method of claim 15, wherein the adjusting the focal length comprises moving the pinhole aperture with respect to the detector assembly.

22. The method of claim 15, wherein a distance from a subject to the pinhole aperture is adjusted based on sensitivity.

23. A method of imaging a volume, comprising:

positioning at least a portion of a subject in a field of view of a single photon emission computed tomography system;

collimating gamma rays emitted from the subject using a plurality of pinhole-detector modules, each pinhole-detector module comprising a collimator having one or more pinhole apertures and a detector assembly;

detecting gamma rays that pass through the one or more pinhole apertures with the corresponding detector assembly;

generating one or more signals in response to the detected gamma rays; and independently adjusting a focal length for two or more of the pinhole-detector modules based on the one or more generated signals.

24. The method of claim 23, comprising:

after the adjusting the focal length, collimating additional gamma rays emitted from the subject using the one or more pinhole-detector modules;

detecting the additional gamma rays that pass through the collimator assembly; and generating one or more images based on the additional gamma rays that were detected.

25. The method of claim 23, comprising adjusting an orientation of at least one of the pinhole-detector modules with respect to the subject.

26. The method of claim 23, comprising adjusting distance of at least one of the pinhole-detector modules with respect to the subject.

* * * * *